United States Patent
Yuan

(10) Patent No.: US 8,012,992 B2
(45) Date of Patent: Sep. 6, 2011

(54) AZA-INDOLES AND RELATED COMPOUNDS HAVING SPHINGOSINE-1-PHOSPHATE (S1P) RECEPTOR ANTAGONIST BIOLOGICAL ACTIVITY

(75) Inventor: Haiqing Yuan, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 158 days.

(21) Appl. No.: 12/493,463

(22) Filed: Jun. 29, 2009

(65) Prior Publication Data
US 2009/0325970 A1 Dec. 31, 2009

Related U.S. Application Data

(60) Provisional application No. 61/133,648, filed on Jun. 30, 2008.

(51) Int. Cl.
C07D 471/02 (2006.01)
C07D 491/02 (2006.01)
C07D 513/02 (2006.01)
C07D 515/02 (2006.01)
A61K 31/44 (2006.01)

(52) U.S. Cl. .................................... 514/300; 546/113

(58) Field of Classification Search .................. 546/113; 514/300
See application file for complete search history.

(56) References Cited

U.S. PATENT DOCUMENTS
7,169,787 B2 * 1/2007 Hofgen et al. ............. 514/253.04

FOREIGN PATENT DOCUMENTS
| EP | 2003132 | 12/2008 |
| WO | 2002034747 | * 5/2002 |
| WO | WO 2007095561 | 8/2007 |
| WO | WO 2007116866 | 10/2007 |
| WO | WO 2007129473 | 11/2007 |

OTHER PUBLICATIONS

Richard B. Silverman, Organic Chemistry of Drug Design and Drug Action, 2d Ed., Elsevier Academic Press: Amsterdam, 2004, pp. 496-557.

Hu et al.; Bioorg. Med. Chem. Lett. 2006 16, 4567-4570.

* cited by examiner

*Primary Examiner* — D. Margaret Seaman
*Assistant Examiner* — Niloofar Rahmani
(74) *Attorney, Agent, or Firm* — Doina G. Ene; John E. Wurst; Kevin J. Forrestal

(57) ABSTRACT

The present invention provides compounds are disclosed herein having the formula:

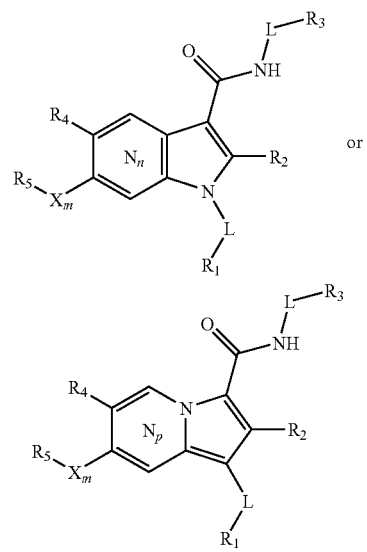

Wherein n is 1 or 2; m is 0 or 1; p is 0, 1 or 2; $R_1$ is aryl, heteroaryl or alkyl;
$R_2$ is $C_{1-6}$ hydrocarbyl, alkylacyl or hydroxyalkyl; $R_3$ is aryl, heteroaryl, or alkyl; $R_4$ is H, OH, —O—($C_{1-6}$ alkyl), —NH—($C_{1-6}$ alkyl), or oxide;
$R_5$ is H, halogen, $C_{1-6}$ alkyl, O—($C_{1-6}$ alkyl), aryl, heteroaryl, —C(=O)($C_{1-6}$ alkyl), substituted or un-substituted oxazolin-2-yl;
X=O, NH, —C(=O)— or —N=CH—; and
Each L is independently alkylene and carbonyl.
Therapeutic methods, compositions, and medicaments related thereto are also disclosed.

9 Claims, No Drawings

AZA-INDOLES AND RELATED COMPOUNDS HAVING SPHINGOSINE-1-PHOSPHATE (S1P) RECEPTOR ANTAGONIST BIOLOGICAL ACTIVITY

CROSS-REFERENCE TO RELATED APPLICATION

This application is based, and claims priority under 35 U.S.C. §120 to U.S. Provisional Patent Application No. 61/133,648 filed on Jun. 30, 2008, and which is incorporated herein by reference.

BACKGROUND

Sphingosine is a compound having the chemical structure shown in the general formula described below, in which $Y^1$ is hydrogen. It is known that various sphingolipids, having sphingosine as a constituent, are widely distributed in the living body including on the surface of cell membranes of cells in the nervous system.

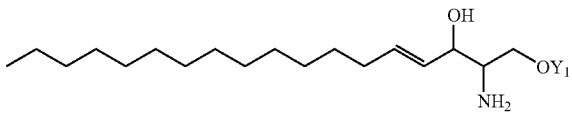

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by sphingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 µM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or sphingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

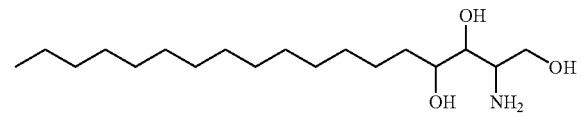

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

DESCRIPTION OF THE INVENTION

Compounds are disclosed herein having the formula:

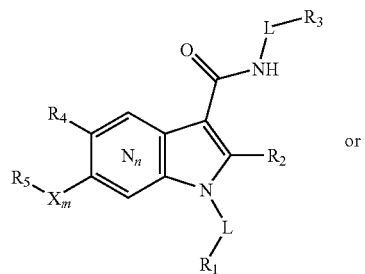

or

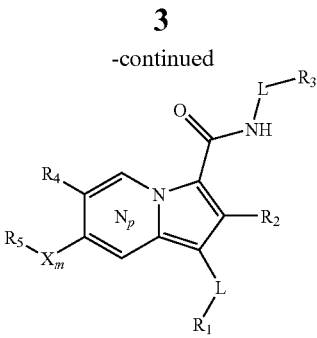

Wherein n is 1 or 2 and indicates the number of enchained nitrogen atoms in the condensed 6 member ring; m is 0 or 1; p is 0, 1 or 2; $R_1$ is aryl, heteroaryl or alkyl;

$R_2$ is selected from the group consisting of $C_{1-6}$ hydrocarbyl, alkylacyl and hydroxyalkyl;

$R_3$ is selected from the group consisting of aryl, heteroaryl, or alkyl; $R_4$ is H, OH, —O—($C_{1-6}$ alkyl), —NH—($C_{1-6}$ alkyl), and oxide;

$R_5$ is selected from the group consisting of H, halogen, $C_{1-6}$ alkyl, O—($C_{1-6}$ alkyl), aryl, heteroaryl, —C(=O)($C_{1-6}$ alkyl), substituted and un-substituted oxazolin-2-yl;

X is selected from the group consisting of O, NH, —C(=O)— and —N=CH—; and

L is selected from the group consisting of alkylene, and carbonyl.

Within the scope of the above general formula, preferably the condensed aza-indole ring moeity is selected from the group of ring systems set forth below:

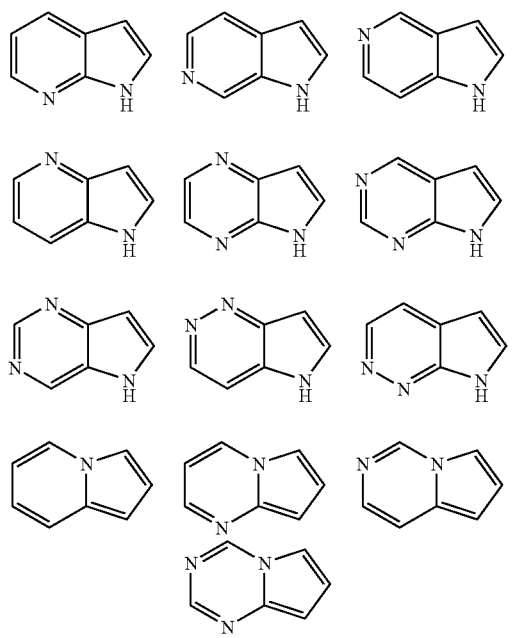

The preferred $R_1$-$R_5$ groups are as follows:

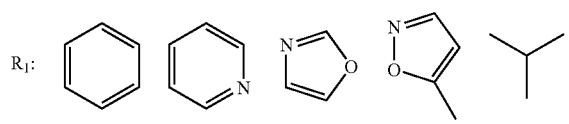

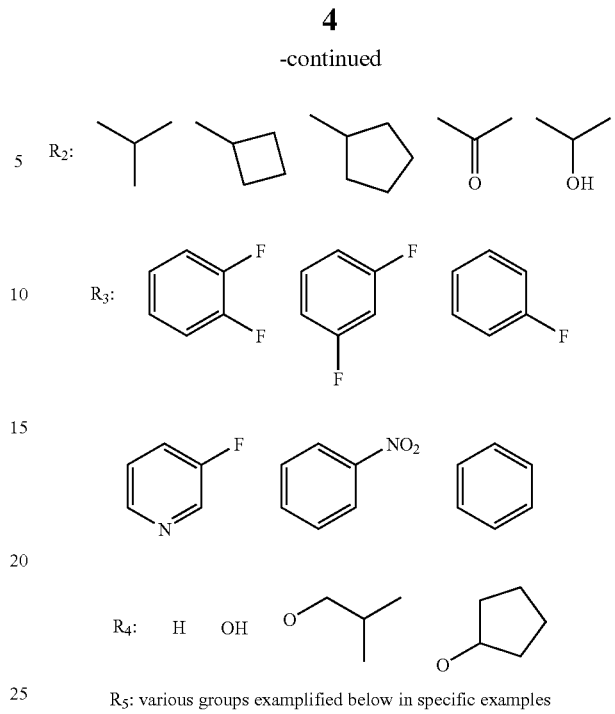

$R_5$: various groups examplified below in specific examples $R_5$ is selected from the group consisting of lower alkyl, e.g. $C_1$-$C_6$ alkyl, i.e. isopropyl, n-butyl, etc. cycloalkyl, e.g. cyclopentyl; thiazolyl; oxazolyl; oxadiazolyl; pyridinyl, oxazolin-2-yl, etc. X is selected from the group consisting of O, C(O), NH, etc. or X is not present.

Specific Examples that illustrate various combinations of $R_4$ and $R_5$—$X_m$ include:

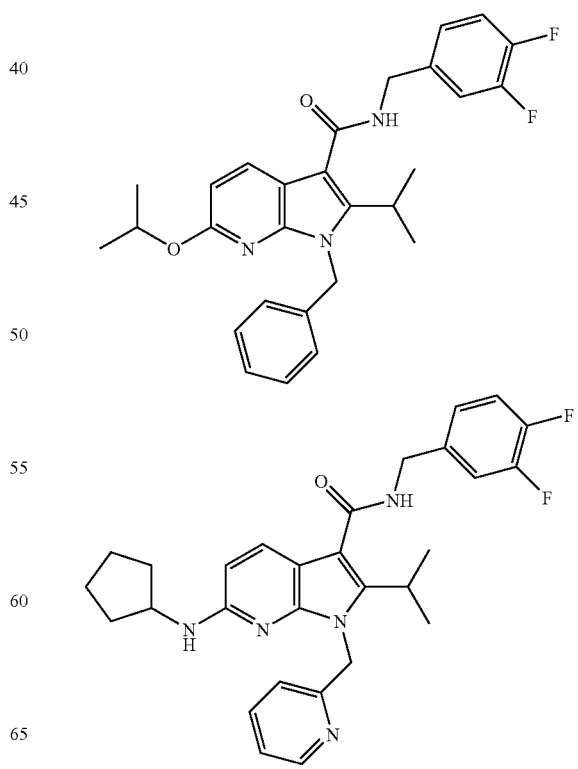

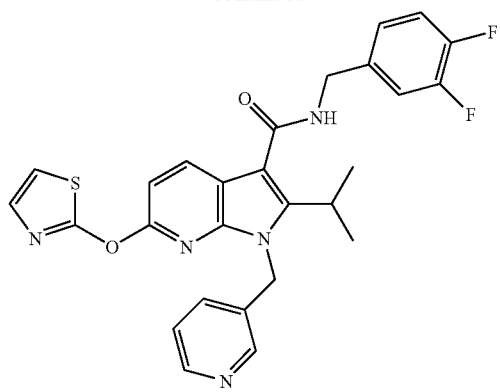
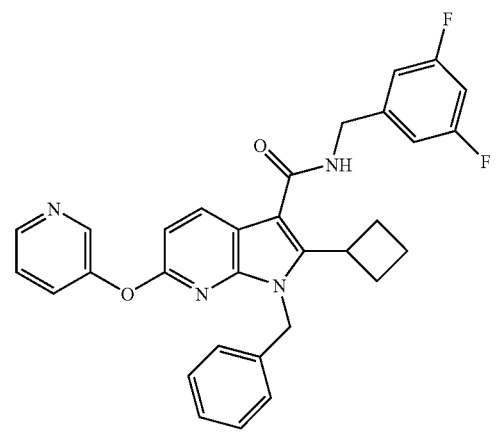
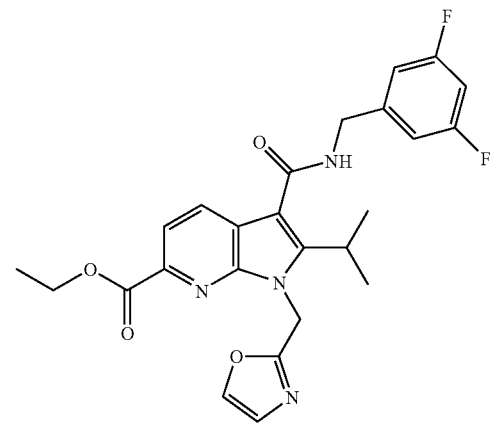
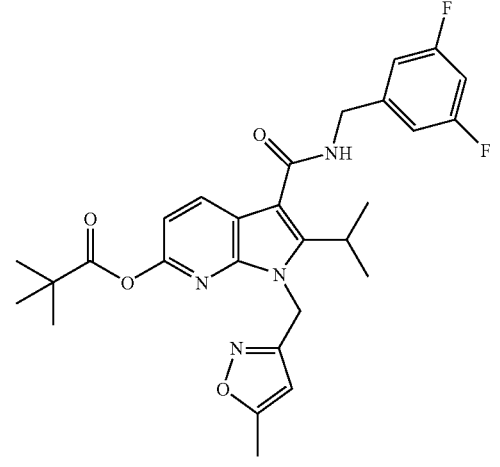
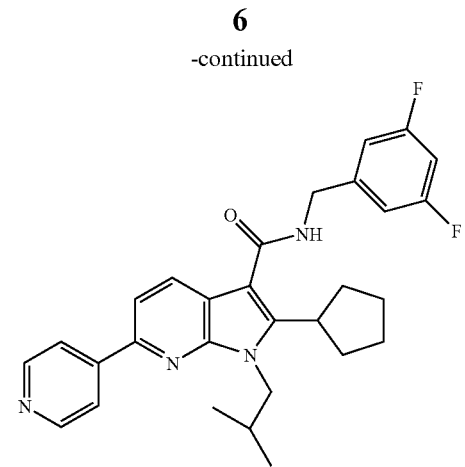
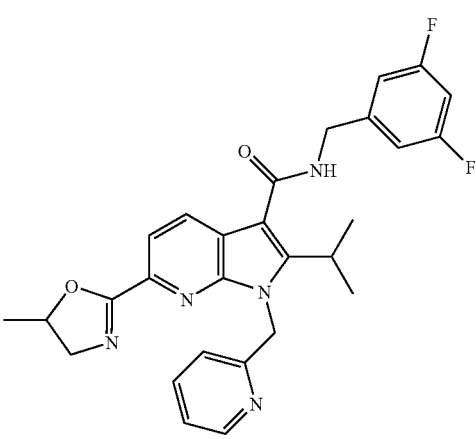
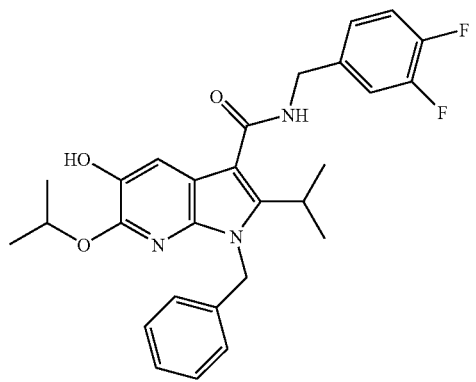
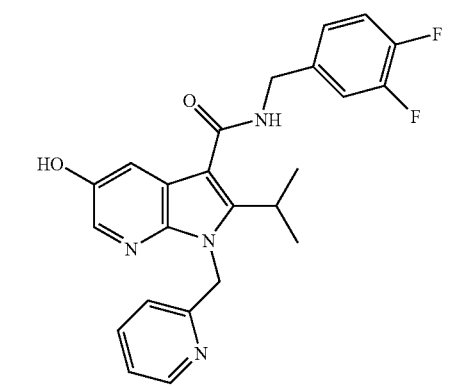

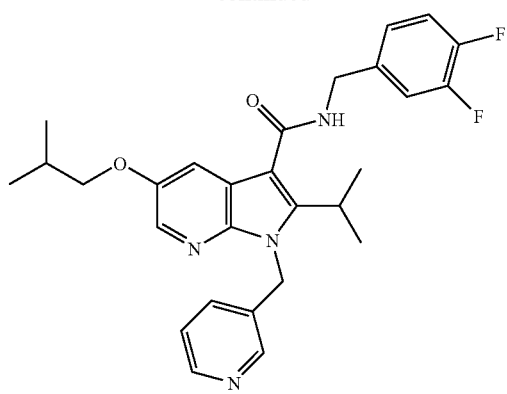
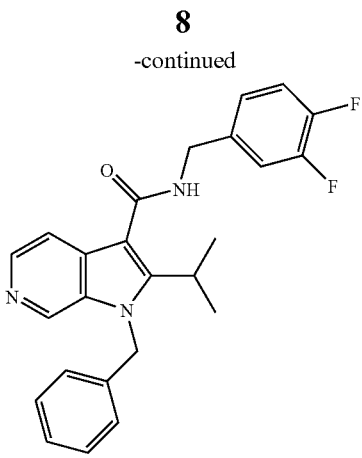
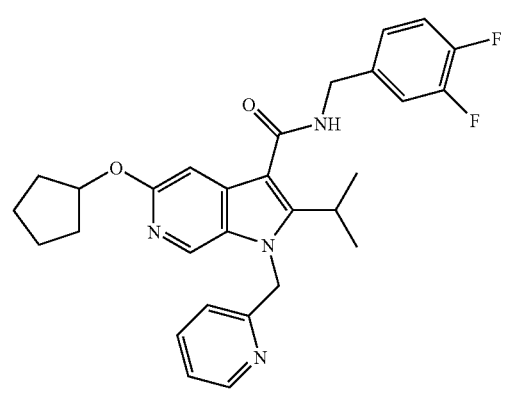
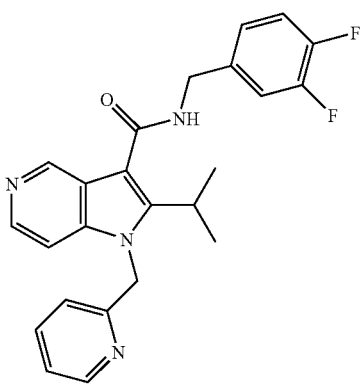
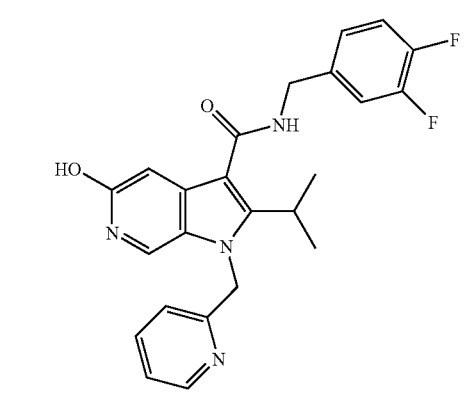
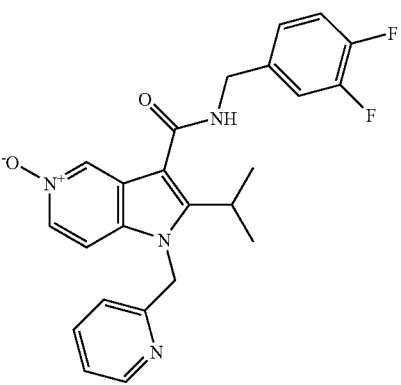
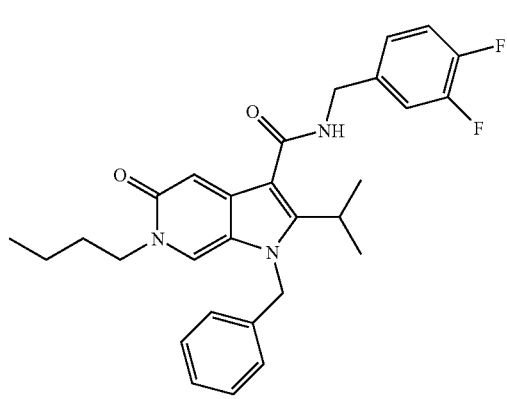
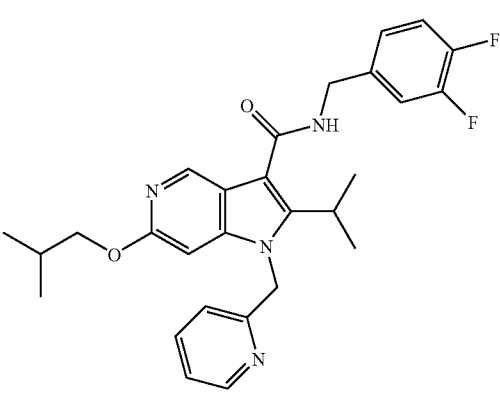

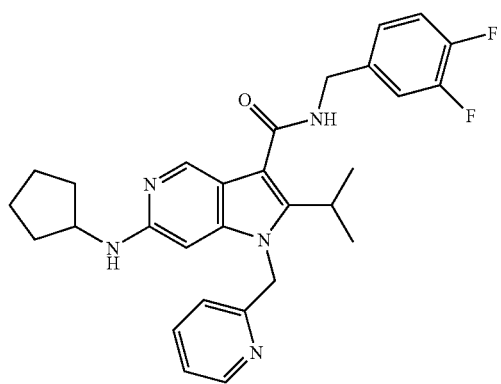
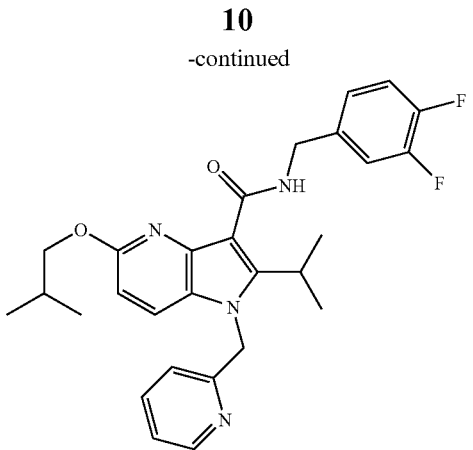
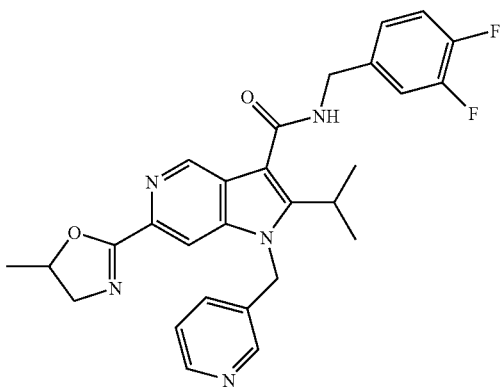
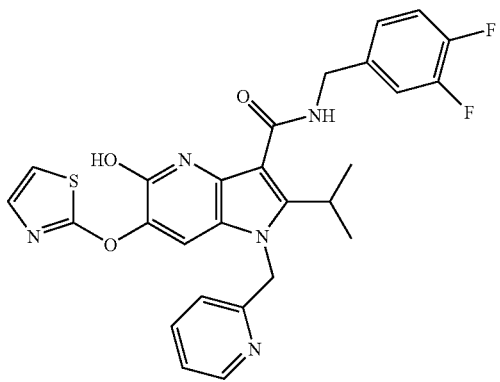
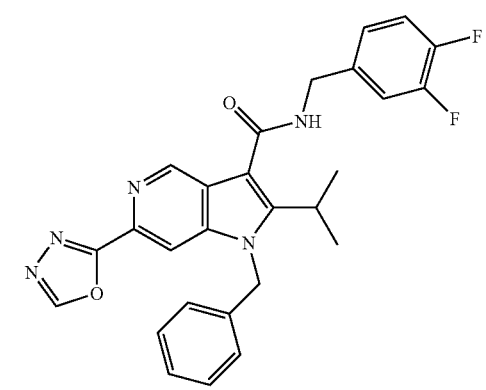
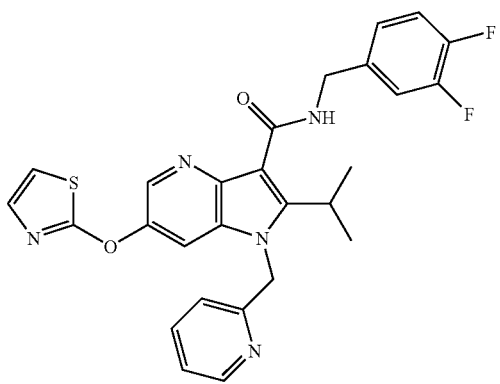
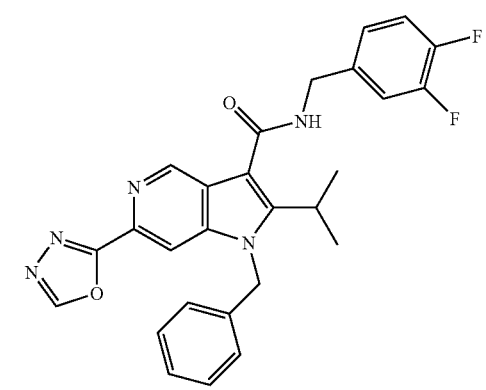
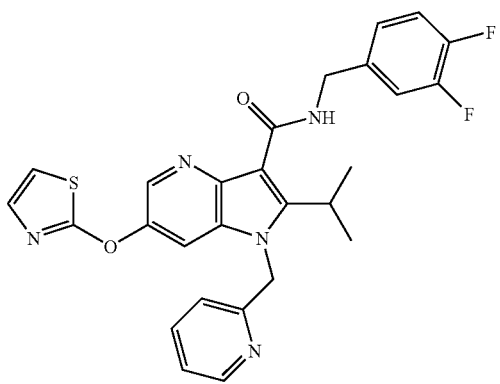

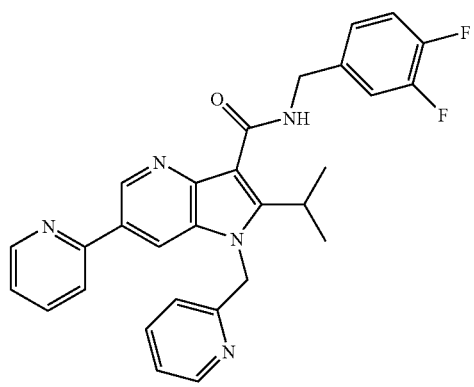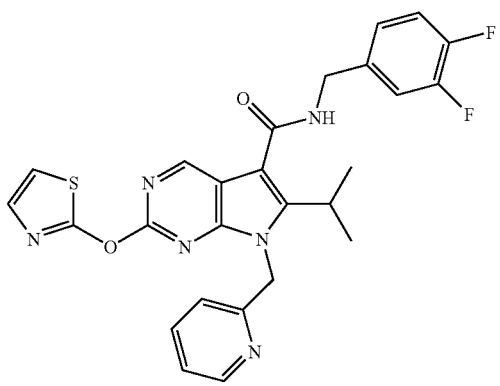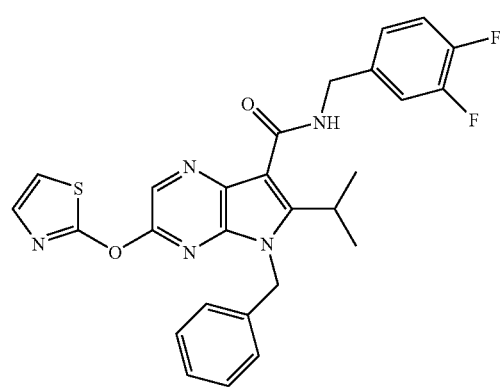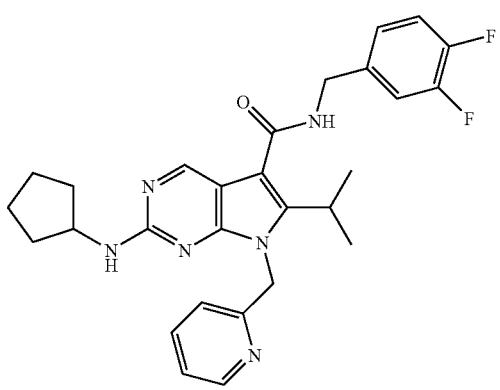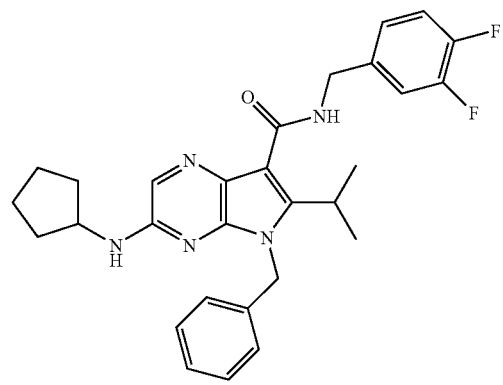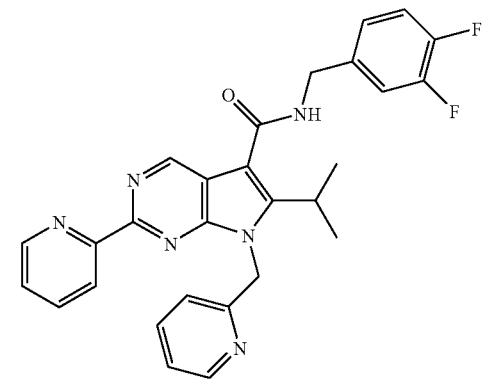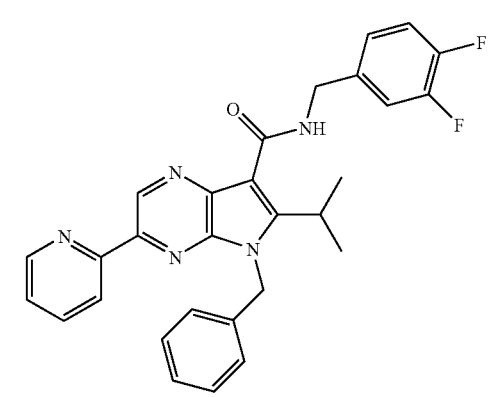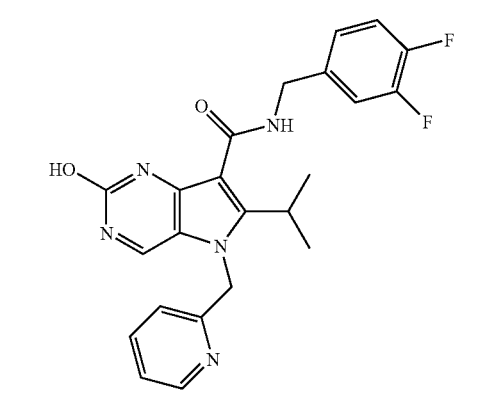

13
-continued

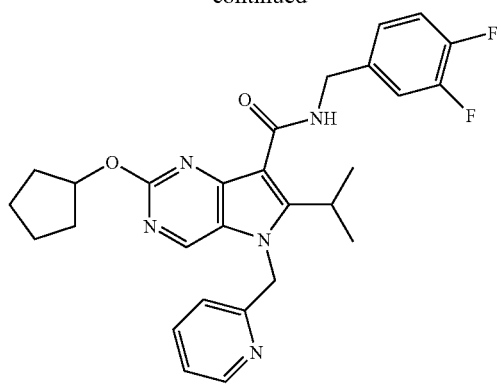

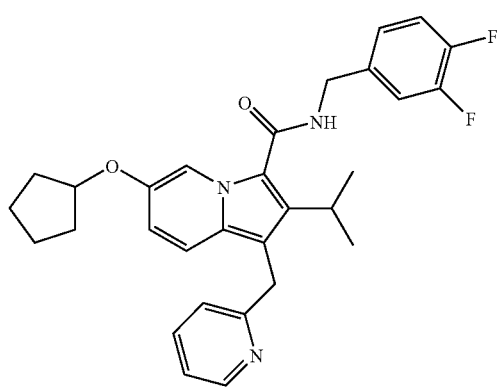

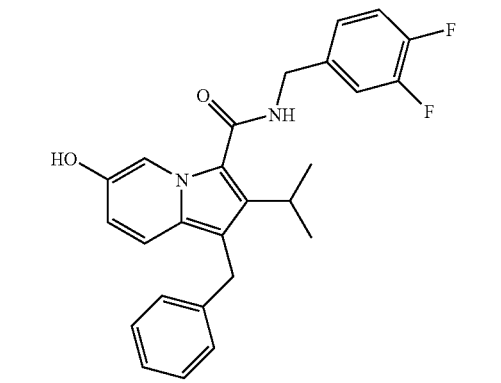

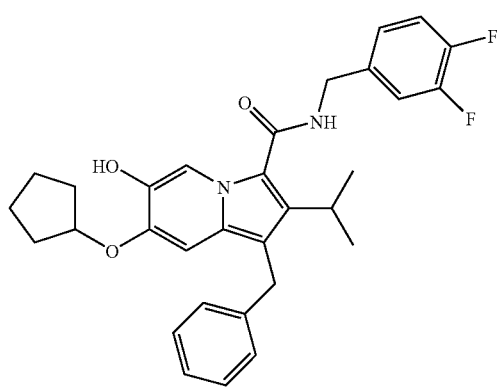

14
-continued

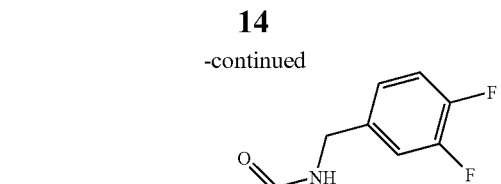

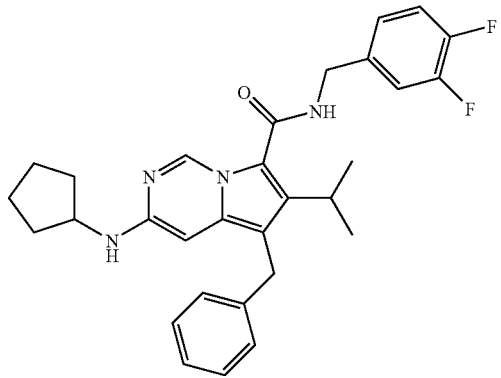

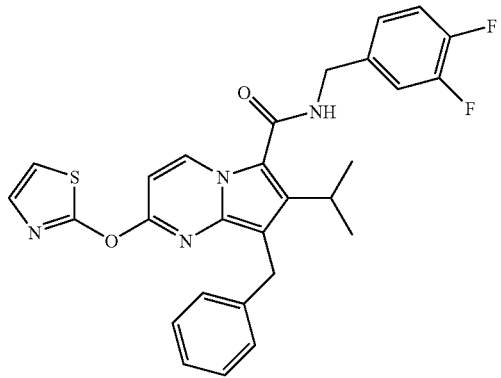

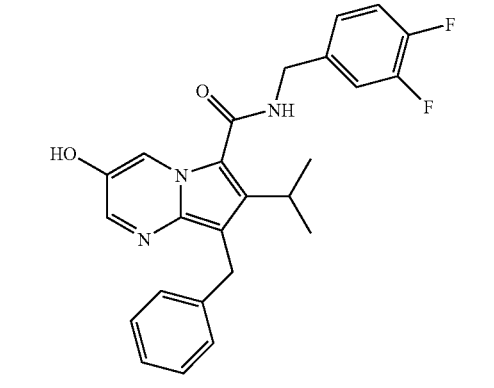

These compounds are useful for the treatment of diseases or conditions such as glaucoma, dry eye, angiogenesis, cardiovascular conditions and diseases, wounds, and pain. The compound is incorporated into a dosage form or a medicament and administered to the mammal, such as a person, in need thereof. Different types of suitable dosage forms and medicaments are well known in the art, and can be readily adapted for delivery of the compounds disclosed herein.

Thus, one embodiment is a method of treating a disease or condition comprising administering a compound disclosed herein to a mammal in need thereof, said disease or condition being selected from: glaucoma, dry eye, angiogenesis, cardiovascular conditions and diseases, wounds, and pain.

Another embodiment is use of a compound disclosed herein in the manufacture of a medicament for the treatment of a disease or condition in a mammal, said disease or condition being selected from: glaucoma, dry eye, angiogenesis, cardiovascular conditions and diseases, wounds, and pain.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Stable means that a compound is sufficiently stable to be stored in a bottle at room temperature under a normal atmosphere for at least 12 hours, or stable enough to be useful for any purpose disclosed herein.

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Hydrocarbyl is a moiety consisting of carbon and hydrogen, including, but not limited to:
a. alkyl, which is hydrocarbyl that contains no double or triple bonds, such as:
   linear alkyl, e.g. methyl, ethyl, n-propyl, n-butyl, n-pentyl, n-hexyl, etc.,
   branched alkyl, e.g. iso-propyl, t-butyl and other branched butyl isomers, branched pentyl isomers, etc.,
   cycloalkyl, e.g. cyclopropyl, cyclobutyl, cyclopentyl, cyclohexyl, etc.,
   combinations of linear, branched, and/or cycloalkyl;
b. alkenyl, which is hydrocarbyl having 1 or more double bonds, including linear, branched, or cycloalkenyl
c. alkynyl, which is hydrocarbyl having 1 or more triple bonds, including linear, branched, or cycloalkynyl;
d. combinations of alkyl, alkenyl, and/or akynyl $C_{1-6}$ hydrocarbyl is hydrocarbyl having 1, 2, 3, 4, 5, or 6 carbon atoms.

$C_{1-6}$ alkyl is alkyl having 1, 2, 3, 4, 5, or 6, carbon atoms such as methyl, ethyl, propyl isomers, butyl isomers, pentyl isomer, and hexyl isomers, etc.

Aryl is an aromatic ring or ring system such as phenyl, naphthyl, biphenyl, and the like. Heteroaryl is an aromatic ring or ring system containing one or more O, N, or S heteroatoms. Both aryl and heteroaryl may be substituted or unsubstituted, and unless otherwise indicated, "aryl" and "heteroaryl" should be taken to mean "substituted or unsubstituted aryl" and "substituted or unsubstituted heteroaryl." Similarly, unless otherwise indicated, any specific aryl or heteroaryl ring such as "phenyl," "pyridinyl," "thienyl," "furyl," etc., should be taken to mean "substituted or unsubstituted phenyl," "substituted or unsubstituted pyridinyl," "substituted or unsubstituted thienyl," "substituted or unsubstituted furyl," etc.

Examples of substituents may include the following, subject to the constraints defined herein for that particular moiety or substituent:

A. Hydrocarbyl, including, but not limited to:
a. alkyl, such as:
   linear alkyl, e.g. methyl, ethyl, n-propyl, n-butyl, n-pentyl, n-hexyl, etc.,
   branched alkyl, e.g. iso-propyl, t-butyl and other branched butyl isomers, branched pentyl isomers, etc.,
   cycloalkyl, e.g. cyclopropyl, cyclobutyl, cyclopentyl, cyclohexyl, etc.,
   combinations of linear, branched, and/or cycloalkyl;
b. alkenyl, which is hydrocarbyl having 1 or more double bonds, including linear, branched, or cycloalkenyl
c. alkynyl, which is hydrocarbyl having 1 or more triple bonds, including linear, branched, or cycloalkynyl;
d. combinations of alkyl, alkenyl, and/or akynyl B. alkyl-CN, such as —$CH_2$—CN, —$(CH_2)_2$—CN; —$(CH_2)_3$—CN, and the like;

C. Hydroxy, —OH

D. hydroxyalkyl, i.e. alkyl-OH, such as hydroxymethyl, hydroxyethyl, and the like;

E. ether substituents, including —O-alkyl, alkyl-O-alkyl, and the like;

F. thioether substituents, including —S-alkyl, alkyl-S-alkyl, and the like;

G. amine substituents, including —$NH_2$, —NH-alkyl,-N-alkyl$^1$alkyl$^2$ (i.e., alkyl$^1$ and alkyl$^2$ are the same or different, and both are attached to N), alkyl-$NH_2$, alkyl-NH-alkyl, alkyl-N-alkyl$^1$alkyl$^2$, and the like;

H. aminoalkyl, meaning alkyl-amine, such as aminomethyl (—$CH_2$-amine), aminoethyl, and the like;

I. ester substituents, including —$CO_2$-alkyl, —$CO_2$-phenyl, etc.;

J. other carbonyl substituents, including aldehydes; ketones, such as acyl, including, acetyl, propionyl, and benzoyl substituents are contemplated;

K. fluorocarbons or hydrofluorocarbons such as —$CF_3$, —$CH_2CF_3$, etc.; and

L. other nitrogen containing substituents such as —CN and —$NO_2$,

M. other sulfur containing substituents such as sulfide, sulfonyl or sulfoxide;

N. aryl;

O. combinations of the above are also possible, subject to the constraints defined;

P. Alternatively, a substituent may be —F, —Cl, —Br, or —I.

When $R_1$, $R_3$, $R_4$ or $R_5$ is heteroaryl, the formula thereof, including both the ring and any substituents, may be $C_{1-6}H_{0-11}N_{0-3}O_{0-2}S_{0-2}F_{0-1}Cl_{0-1}Br_{0-1}$. Thus, if $R_1$, $R_3$, $R_4$ or $R_5$ is heteroaryl, it consists of from 1 to 6 carbon atoms, from 0 to 11 hydrogen atoms, from 0 to 3 nitrogen atoms, from 0 to 2 oxygen atoms, from 0 to 2 sulfur atoms, from 0 to 1 fluorine atoms, from 0 to 1 chlorine atoms, and from 0 to 1 bromine atoms.

The structures below are examples of useful heteroaryl moieties for $R_1$, $R_3$, $R_4$ or $R_5$.

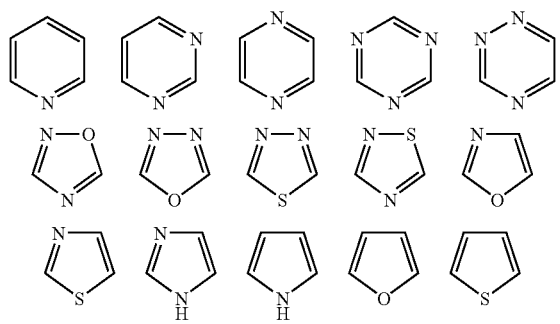

The structures below are examples of useful aryl moieties for $R_1$, $R_3$, $R_4$ or $R_5$

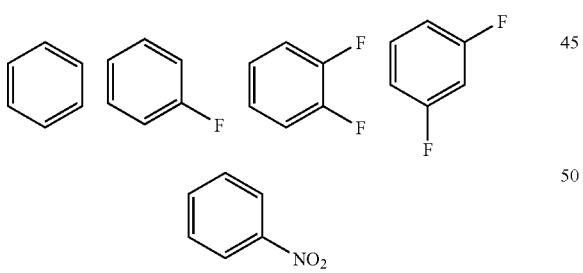

EXPERIMENTAL

Scheme 1<sup>a</sup>

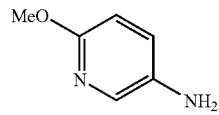

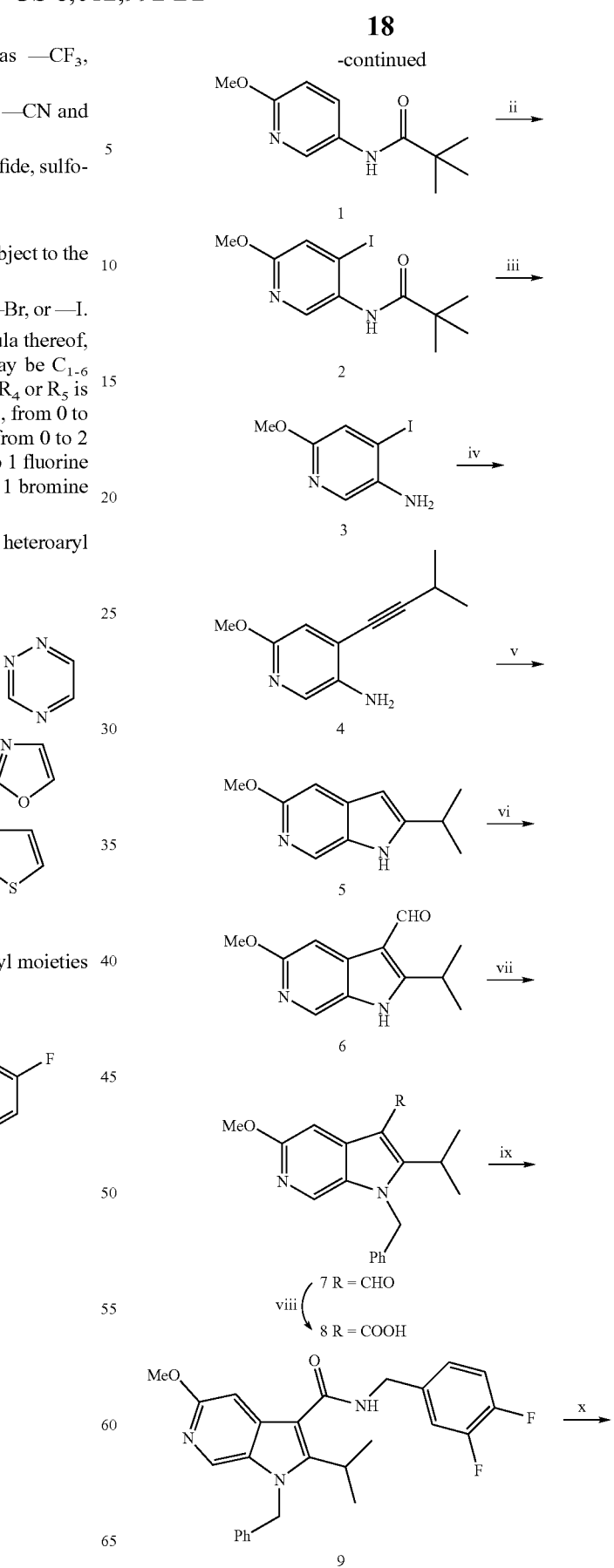

19

-continued

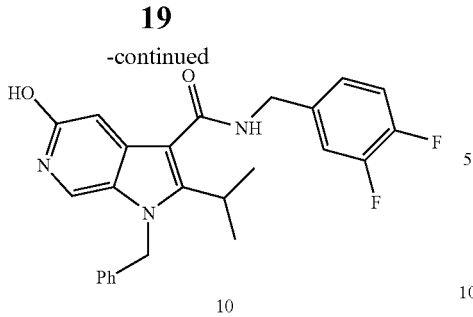

10

*Reagents and conditions: (i) Piv-Cl, Et₃N, CH₂Cl₂; (ii) t-BuLi, THF, -78° C., then I₂; (iii) 10% H₂SO₄, reflux; (iv) 3-methyl-1-butyne, CuI, Pd(PPh₃)₂Cl₂, Et₃N; (v) KOtBu, NMP, 140° C.; (vi) POCl₃, DMF, 90° C., 2 h; (vii) BnBr, K₂CO₃, DMF; (viii) NaClO₂, NaH₂PO₄, isobutene, t-BuOH, H₂O; (ix) 3,4-difluorobenzylamine, EDC, DMAP, Et₃N, CH₂Cl₂; (x) 48% HBr, HOAc, 120° C., 5 h.

Example 1

N-(6-methoxypyridin-3-yl)pivalamide (Compound 1). To a solution of 6-methoxy-pyridin-3-amine (Aldrich, 10.0 g, 77 mmol) in anhydrous CH$_2$Cl$_2$ (100 ml) at 0° C. was added Et$_3$N (13.9 ml, 100.1 mmol) and a solution of pivaloyl chloride (10.5 ml, 84.7 mmol) in CH$_2$Cl$_2$ (20 ml). The mixture was stirred at 0° C. for 10 min and at room temperature for 2 h. After quenched with ice, the reaction was diluted with CH$_2$Cl$_2$, washed with 1M NaOH, brine, dried over Na$_2$SO$_4$, and concentrated in vacuo. The residue was purified by chromatography on silica gel (0→30% EtOAc-hexanes) to yield the title compound as orange solid.

1H NMR (300 MHz, CHLOROFORM-d) δ ppm 1.32 (s, 9H), 3.92 (s, 3H), 6.73 (d, J=9.1 Hz, 1H), 7.23 (s, 1H), 7.91 (dd, J=8.9, 2.8 Hz, 1H), 8.13 (d, J=2.6 Hz, 1H).

Example 2

N-(4-iodo-6-methoxypyridin-3-yl)pivalamide (Compound 2). To a solution of N-(6-methoxypyridin-3-yl)pivalamide (Compound 1, 7.4 g, 35.6 mmol) in anhydrous THF (200 ml) at −78° C. under argon was added t-BuLi (1.7 M in pentane, 52 ml, 89.0 mmol) slowly. After stirred at −78° C. for 1 h, a solution of I$_2$ (22.6 g, 89.0 mmol) in anhydrous THF (100 ml) at −78° C. was cannulated into the reaction over 20 min and the reaction was stirred for 15 min at −78° C. The cooling bath was then removed and the reaction stirred for 30 min, quenched cautiously with ice, extracted with CH$_2$Cl$_2$. The organic layer was dried over Na$_2$SO$_4$, and concentrated in vacuo. The residue was purified by chromatography on silica gel (0→30% EtOAc-hexanes) to yield the title compound.

1H NMR (300 MHz, CHLOROFORM-d) δ ppm 1.37 (s, 9H), 3.92 (s, 3H), 7.25 (s, 1H), 7.38 (s, 1H), 8.71 (s, 1H).

Example 3

4-Iodo-6-methoxypyridin-3-amine (Compound 3). A solution of N-(4-iodo-6-methoxypyridin-3-yl)pivalamide (Compound 2, 2.33 g, 7.0 mmol) in 10% H$_2$SO$_4$ (70 ml) was heated to reflux at 120° C. for 5 h. The mixture was cooled to 0° C. and was quenched cautiously with solid NaOH (10 g), extracted with EtOAc (×2). The combined organic layer was washed with brine, dried over Na$_2$SO$_4$, and concentrated in vacuo. The residue was purified by chromatography on silica gel (0→30% EtOAc-hexanes) to yield the title compound as off-white solid.

1H NMR (300 MHz, CHLOROFORM-d) δ ppm 3.72 (s, 2H), 3.85 (s, 3H), 7.15 (s, 1H), 7.65 (s, 1H).

Example 4

6-Methoxy-4-(3-methylbut-1-ynyl)pyridin-3-amine (Compound 4). To a solution of 4-iodo-6-methoxypyridin-3-amine (Compound 3, 845 mg, 3.4 mmol) in Et$_3$N (12 ml) in a re-sealable pressure tube was added Pd(PPh$_3$)$_2$Cl$_2$ (24 mg, 0.034 mmol), CuI (7.0 mg, 0.034 mmol), and 3-methyl-1-butyne (0.66 ml, 6.8 mmol). The mixture was stirred at room temperature for 20 h and the solvent was removed in vacuo. The residue was purified by chromatography on silica gel (0→30% EtOAc-hexanes) to yield the title compound as beige solid.

1H NMR (300 MHz, CHLOROFORM-d) δ ppm 1.30 (d, J=6.7 Hz, 6H), 2.76-2.93 (m, 1H), 3.76 (s, 2H), 3.85 (s, 3H), 6.64 (s, 1H), 7.69 (s, 1H).

Example 5

2-Isopropyl-5-methoxy-1H-pyrrolo[2,3-c]pyridine (Compound 5). To a solution of 6-methoxy-4-(3-methylbut-1-ynyl)pyridin-3-amine (Compound 4, 588 mg, 3.1 mmol) in N-methylpyrrolidone (10 ml) was added KOtBu (0.87 g, 7.8 mmol) at room temperature. The mixture was heated to 140° C. for 0.5 h and cooled to room temperature, quenched with H$_2$O, extracted with EtOAc. The organic layer was washed with brine, dried over Na$_2$SO$_4$, and concentrated in vacuo. The residue was purified by chromatography on silica gel (0→50% EtOAc-hexanes) to yield the title compound as light brown syrup.

1H NMR (300 MHz, CHLOROFORM-d) δ ppm 1.36 (d, J=7.0 Hz, 6H), 2.97-3.16 (m, 1H), 3.95 (s, 3H), 6.15 (m, 1H), 6.81 (m, 1H), 8.21 (s, 1H), 8.26 (s, 1H).

Example 6

2-Isopropyl-5-methoxy-1H-pyrrolo[2,3-c]pyridine-3-carbaldehyde (Compound 6). POCl$_3$ (1.1 ml, 12.5 mmol) was added to anhydrous DMF (10 ml) at 0° C. slowly and stirred for 0.5 h. This was added to a solution of 2-isopropyl-5-methoxy-1H-pyrrolo[2,3-c]pyridine (Compound 5, 468 mg, 2.5 mmol) in anhydrous DMF (15 ml) at room temperature. The mixture was then heated to 90° C. for 2 h and cooled to room temperature, quenched cautiously with aqueous Na$_2$CO$_3$, extracted with EtOAc (×4). The combined organic layer was washed with brine, dried over Na$_2$SO$_4$, and concentrated in vacuo. The residue was purified by chromatography on silica gel (0→100% EtOAc-hexanes) to yield the title compound as beige solid.

1H NMR (300 MHz, CHLOROFORM-d) δ ppm 1.48 (d, J=7.0 Hz, 6H), 3.72-3.88 (m, 1H), 3.98 (s, 3H), 7.52 (d, J=0.9 Hz, 1H), 8.35 (d, J=0.9 Hz, 1H), 10.22 (s, 1H).

Example 7

1-Benzyl-2-isopropyl-5-methoxy-1H-pyrrolo[2,3-c]pyridine-3-carbaldehyde (Compound 7). A mixture of 2-isopropyl-5-methoxy-1H-pyrrolo[2,3-c]pyridine-3-carbaldehyde (Compound 6, 110 mg, 0.50 mmol), benzyl bromide (0.18 ml, 1.50 mmol), and K$_2$CO$_3$ (208 mg, 1.50 mmol) in DMF (2.5 ml) was stirred at room temperature for 4 h. The solvent was removed in vacuo and the residue was purified by chromatography on silica gel (50% EtOAc-hexanes) to yield the title compound as yellow solid.

1H NMR (500 MHz, METHANOL-d₄) δ ppm 1.45 (d, J=7.3 Hz, 6H), 3.53-3.70 (m, 1H), 3.92 (s, 3H), 5.62 (s, 2H), 7.06 (d, J=7.8 Hz, 2H), 7.21-7.39 (m, 3H), 7.55 (s, 1H), 8.26 (s, 1H), 10.34 (s, 1H).

Example 8

1-Benzyl-2-isopropyl-5-methoxy-1H-pyrrolo[2,3-c]pyridine-3-carboxylic acid (Compound 8). To a solution of 1-benzyl-2-isopropyl-5-methoxy-1H-pyrrolo[2,3-c]pyridine-3-carbaldehyde (Compound 7, 20 mg, 0.065 mmol) in t-BuOH (1.5 ml) and 2-methyl-2-butene (1 ml) was added a solution of NaH₂PO₄ (94 mg, 0.78 mmol) and NaClO₂ (80%, 73 mg, 0.65 mmol) in H₂O (1.5 ml). The mixture was stirred at room temperature and additional 2-methyl-2-butene and a solution of NaH₂PO₄ and NaClO₂ in H₂O were added at the above ratio every 6-16 h until the progress of the reaction was satisfactory. The reaction mixture was extracted with EtOAc (×3) and the combined organic layer was washed with brine, dried over Na₂SO₄, and concentrated in vacuo. The residue was purified by preparative thin layer chromatography (PTLC) on silica gel (50% EtOAc-hexanes) to yield the title compound.

1H NMR (300 MHz, METHANOL-d₄) δ ppm 1.39 (d, J=7.3 Hz, 6H), 3.90 (s, 3H), 3.92-4.03 (m, 1H), 5.62 (s, 2H), 7.00 (dd, J=8.1, 1.3 Hz, 2H), 7.20-7.37 (m, 3H), 7.43 (s, 1H), 8.15 (s, 1H).

Example 9

1-Benzyl-N-(3,4-difluorobenzyl)-2-isopropyl-5-methoxy-1H-pyrrolo[2,3-c]pyridine-3-carboxamide (Compound 9). To a solution of 1-benzyl-2-isopropyl-5-methoxy-1H-pyrrolo[2,3-c]pyridine-3-carboxylic acid (Compound 8, 6.0 mg, 0.019 mmol) and 3,4-difluorobenzylamine (7.0 l, 0.057 mmol) in CH₂Cl₂ (1.0 ml) was added EDC (5.5 mg, 0.029 mmol), DMAP (3.5 mg, 0.029 mmol), and Et₃N (25 l). The mixture was stirred at room temperature for 16 h and was directly purified by preparative thin layer chromatography (PTLC) on silica gel (50% EtOAc-hexanes) to yield the title compound.

1H NMR (300 MHz, METHANOL-d₄) δ ppm 1.35 (d, J=7.0 Hz, 6H), 3.38-3.59 (m, 1H), H), 3.86 (s, 3H), 4.57 (s, 2H), 5.56 (s, 2H), 6.91 (s, 1H), 6.98 (dd, J=7.9, 1.5 Hz, 2H), 7.17-7.41 (m, 6H), 8.14 (s, 1H).

Example 10

1-Benzyl-N-(3,4-difluorobenzyl)-5-hydroxy-2-isopropyl-1H-pyrrolo[2,3-c]pyridine-3-carboxamide (Compound 10). A solution of 1-benzyl-N-(3,4-difluorobenzyl)-2-isopropyl-5-methoxy-1H-pyrrolo[2,3-c]pyridine-3-carboxamide (Compound 9, 7.0 mg, 0.016 mmol) in HBr (48%, 0.5 ml) and HOAc (1.0 ml) was heated to 120° C. for 5 h. The solvent was removed in vacuo and the residue was purified by preparative thin layer chromatography (PTLC) on silica gel (10% MeOH—CH₂Cl₂) to yield the title compound.

1H NMR (300 MHz, CHLOROFORM-d) δ ppm 1.41 (d, J=7.0 Hz, 6H), 3.70-3.86 (m, 1H), 4.58 (d, J=5.6 Hz, 2H), 5.28 (s, 2H), 6.33 (s, 1H), 6.64 (s, 1H), 6.96 (d, J=7.3 Hz, 2H), 7.06-7.35 (m, 6H), 7.41 (s, 1H).

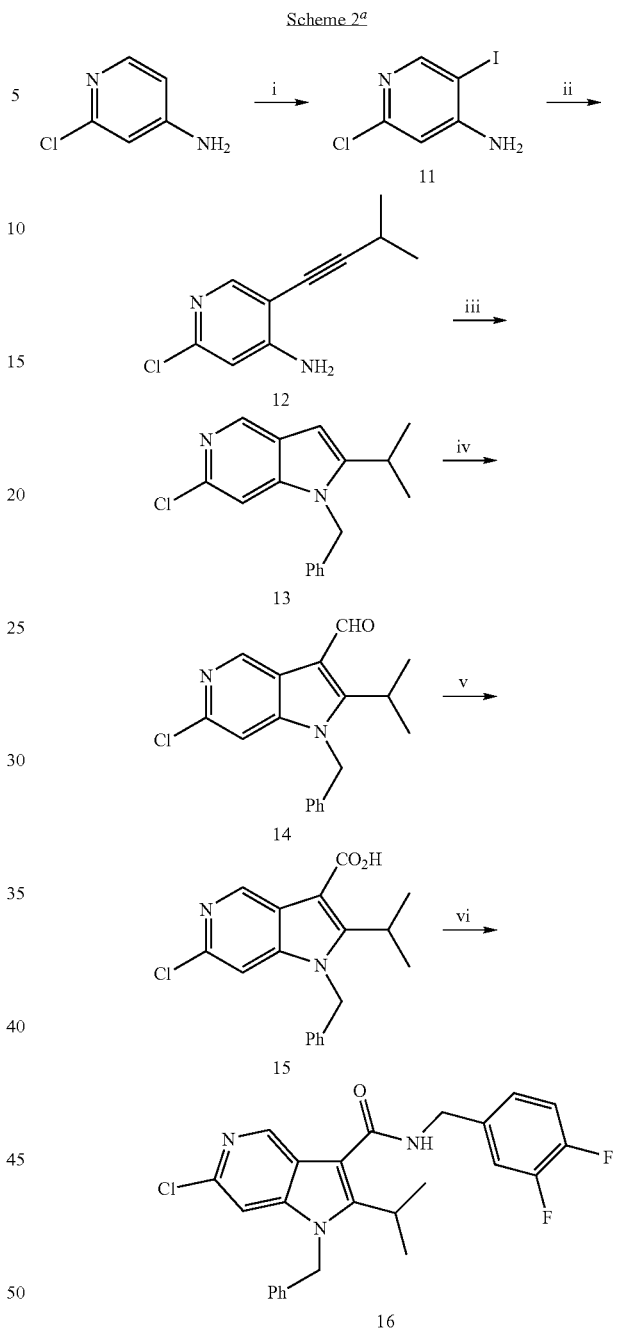

Scheme 2ᵃ

ᵃReagents and conditions: (i) ICl, KOAc, HOAc (ii) 3-methyl-1-butyne, CuI, Pd(PPh₃)₂Cl₂, Et₃N; (iii) KOtBu, NMP 160° C.; then BnBr, THF, DMF, rt. (iv) POCl₃, DMF; (v) NaClO₂, NaH₂PO₃, isobutene, t-BuOH, H₂O; (vi) 3,4-difluorobenzylamine, EDC, DMAP, DMF.

Example 11

2-Chloro-5-iodopyridin-4-amine (Compound 11). This compound was prepared according to the following literature procedure: Hu et al.; *Bioorg. Med. Chem. Lett.* 2006 16, 4567-4570.

Example 12

2-Chloro-5-(3-methylbut-1-ynyl)pyridin-4-amine (Compound 12). To a solution of 2-chloro-5-iodopyridin-4-amine (Compound 11, 2.55 g, 10.0 mmol) in Et$_3$N (35 ml) was added Pd(PPh$_3$)$_2$Cl$_2$ (70 mg, 0.10 mmol), CuI (19 mg, 0.10 mmol), and 3-methyl-1-butyne (1.2 ml, 12 mmol). The reaction was stirred at room temperature for 20 h and was quenched with H$_2$O, extracted with EtOAc (×2). The combined organic layer was washed with brine, dried over Na$_2$SO$_4$, and concentrated in vacuo. The residue was purified by chromatography on silica gel (0→30% EtOAc-hexanes) to yield the title compound as an off-white solid.

1H NMR (300 MHz, CHLOROFORM-d) δ ppm 1.29 (d, J=6.7 Hz, 6H), 2.71-3.02 (m, 1H), 4.70 (s, 2H), 6.57 (s, 1H), 8.08 (s, 1H).

Example 13

1-Benzyl-6-chloro-2-isopropyl-1H-pyrrolo[3,2-c]pyridine (Compound 13). To a solution of 2-chloro-5-(3-methyl-but-1-ynyl)pyridin-4-amine (Compound 12, 0.82 g, 4.2 mmol) in NMP (10 ml) was added KOtBu (2.40 g, 21 mmol). The mixture was stirred at 160° C. for 6 h and was cooled to room temperature, diluted with THF (10 ml) and DMF (15 ml). Benzyl bromide (0.50 ml, 4.2 mmol) was added. The mixture was stirred at room temperature for 16 h and was quenched with H$_2$O, extracted with EtOAc (×2). The combined organic layer was washed with brine, dried over Na$_2$SO$_4$, and concentrated in vacuo. The residue was purified by chromatography on silica gel (0→50% EtOAc-hexanes) to yield the title compound as a white solid.

1H NMR (300 MHz, CHLOROFORM-d) δ ppm 1.28 (d, J=7.0 Hz, 6H), 2.89-3.06 (m, 1H), 5.31 (s, 2H), 6.42 (s, 1H), 6.86-6.94 (m, 2H), 7.07 (s, 1H), 7.21-7.37 (m, 8.58 (s, 1H).

Example 14

1-Benzyl-6-chloro-2-isopropyl-1H-pyrrolo[3,2-c]pyridine-3-carbaldehyde (Compound 14). POCl$_3$ (0.31 ml, 3.42 mmol) was added to anhydrous DMF (5 ml) at 0° C. slowly and stirred for 20 min. To this solution was added a solution of 1-benzyl-6-chloro-2-isopropyl-1H-pyrrolo[3,2-c]pyridine (Compound 13, 195 mg, 0.68 mmol) in anhydrous DMF (7 ml) at room temperature. The mixture was stirred at room temperature for 2 h and was then heated to 60° C. for 2 h and 80° C. for 0.5 h. The reaction was cooled to room temperature, quenched cautiously with aqueous Na$_2$CO$_3$, extracted with EtOAc (×2). The combined organic layer was washed with brine, dried over Na$_2$SO$_4$, and concentrated in vacuo. The residue was purified by chromatography on silica gel (0→30% EtOAc-hexanes) to yield the title compound.

1H NMR (300 MHz, CHLOROFORM-d) δ ppm 1.46 (d, J=7.3 Hz, 6H), 3.35-3.57 (m, 1H), 5.40 (s, 2H), 6.95 (dd, J=7.5, 2.2 Hz, 2H), 7.17 (s, 1H), 7.29-7.41 (m, 3H), (s, 1H), 10.46 (s, 1H).

Example 15

1-Benzyl-6-chloro-2-isopropyl-1H-pyrrolo[3,2-c]pyridine-3-carboxylic acid (Compound 15). To a solution of 1-benzyl-6-chloro-2-isopropyl-1H-pyrrolo[3,2-c]pyridine-3-carbaldehyde (Compound 14, 146 mg, 0.47 mmol) in t-BuOH (15 ml) and 2-methyl-2-butene (10 ml) was added a solution of NaH$_2$PO$_4$ (1.41 g, 11.8 mmol) and NaClO$_2$ (80%, 1.05 g, 9.3 mmol) in H$_2$O (10 ml). The mixture was stirred at room temperature for 16 h and was extracted with EtOAc (×2). The combined organic layer was washed with brine, dried over Na$_2$SO$_4$, and concentrated in vacuo. The residue was purified by chromatography on silica gel (0→100% EtOAc-hexanes, then 0→30% MeOH—CH$_2$Cl$_2$) to yield the title compound as a yellow solid.

1H NMR (300 MHz, DMSO-d$_6$) δ ppm 1.27 (d, J=7.0 Hz, 6H), 3.65-3.91 (m, 1H), (s, 2H), 6.85-7.03 (m, 2H), 7.19-7.43 (m, 3H), 7.71 (s, 1H), 8.97 (s, 1H), 12.68 (s, 1H).

Example 16

1-Benzyl-6-chloro-N-(3,4-difluorobenzyl)-2-isopropyl-1H-pyrrolo[3,2-c]pyridine-3-carboxamide (Compound 16). To a solution of 1-benzyl-6-chloro-2-isopropyl-1H-pyrrolo[3,2-c]pyridine-3-carboxylic acid (Compound 15, 138 mg, 0.42 mmol) and 3,4-difluorobenzylamine (0.15 ml, 1.26 mmol) in DMF (4.0 ml) was added EDC (121 mg, 0.63 mmol) and DMAP (77 mg, 0.63 mmol). The mixture was stirred at room temperature for 16 h and was diluted with EtOAc, washed with H$_2$O and brine, dried over Na$_2$SO$_4$, and concentrated in vacuo. The residue was purified by chromatography on silica gel (0→100% EtOAc-hexanes) to yield the title compound as a light yellow solid.

1H NMR (300 MHz, CHLOROFORM-d) δ ppm 1.36 (d, J=7.0 Hz, 6H), 3.42-3.54 (m, 1H), 4.65 (d, J=6.2 Hz, 2H), 5.33 (s, 2H), 6.86 (dd, J=7.2, 2.2 Hz, 2H), 6.97-6.99 (m, 1H), 7.01 (t, J=6.0 Hz, 1H), 7.09-7.17 (m, 2H), 7.21-7.32 (m, 4H), 8.57 (s, 1H).

The foregoing description details specific methods and compositions that can be employed to practice the present invention, and represents the best mode contemplated. Thus, however detailed the foregoing may appear in text, it should not be construed as limiting the overall scope hereof; rather, the ambit of the present invention was to be governed only by the lawful construction of the appended claims.

What is claimed is:
1. A compound having the formula:

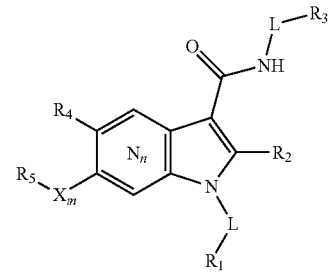

wherein n is 1 and indicates the number of enchained nitrogen atoms in the condensed 6 member ring; m is 0 or 1; R$_1$ is aryl, heteroaryl or alkyl;
R$_2$ is selected from the group consisting of isopropyl, cyclobutyl and cyclopentyl;
R$_3$ is selected from the group consisting of aryl, heteroaryl, or alkyl; R$_4$ is H, OH, —O—(C$_{1-6}$ alkyl), —NH—(C$_{1-6}$ alkyl), and oxide;
R$_5$ is selected from the group consisting of H, halogen, C$_{1-6}$ alkyl, O—(C$_{1-6}$ alkyl), aryl, heteroaryl, —C(=O)(C$_{1-6}$ alkyl), substituted and un-substituted oxazolin-2-yl;
X is selected from the group consisting of O, NH, —C(=O)— and —N=CH—; and
L is selected from the group consisting of alkylene, and carbonyl.
2. The compound of claim 1 wherein R$_1$ is selected from the group consisting of phenyl, pyridine-2-yl, pyridine-3-yl, oxazol-2-yl, isoxazol-3-yl, 5-methyl-isoxazol-3-yl and 3-methyl-isoxazol-5-yl and isopropyl.

3. The compound of claim 1 wherein $R_3$ is selected from the group consisting of 3,4-difluorophenyl, 3,5-difluorophenyl, 3-fluorophenyl, 4-fluorophenyl, 3-fluoropyridine-5-yl, 3-nitrophenyl and phenyl.

4. The compound of claim 1 wherein $R_4$ is selected from the group consisting of hydrogen, hydroxyl, isobutoxyl and cyclopentyloxyl.

5. The compound of claim 1 wherein $R_5$ is selected from the group consisting of $C_1$-$C_6$ alkyl, thiazolyl, oxazolyl, oxadiazolyl, thiadiazolyl, pyridinyl, tetrahydrofuranyl, tetrahydropyranyl, $C_1$-$C_6$ alkoxyl, alkylacyl, and substituted or un-substituted oxazolin-2-yl.

6. The compound of claim 1 wherein X is selected from the group consisting of O, C(O) and NH.

7. The compound of claim 6 wherein $R_5$ is selected from the group consisting of propyl, isopropyl, n-butyl, isobutyl, sec-butyl, cyclopropyl, cyclopropylmethyl, cyclobutyl, cyclopentyl, thiazolyl, oxazolyl, oxadiazolyl, thiadiazolyl, pyridinyl, tetrahydrofuranyl, tetrahydropyranyl, $C_1$-$C_6$ alkoxyl, alkylacyl, and substituted or un-substituted oxazolin-2-yl.

8. The compound of claim 1 having a formula:

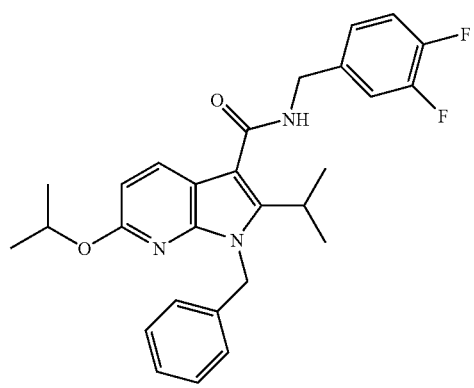

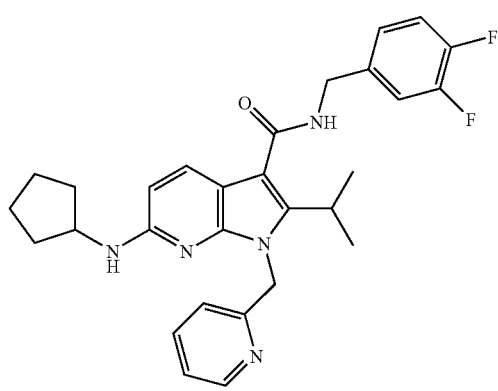

-continued

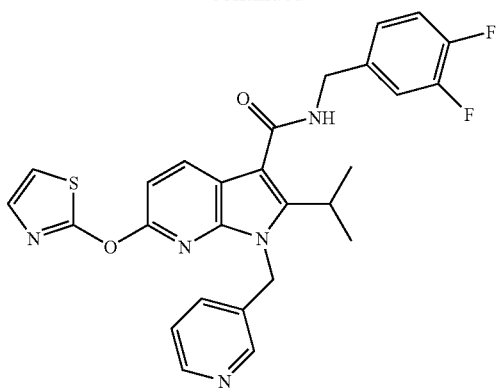

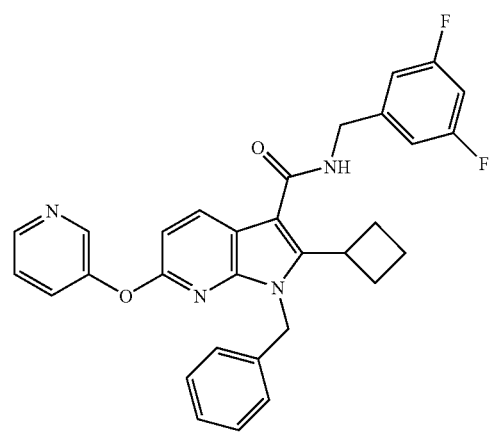

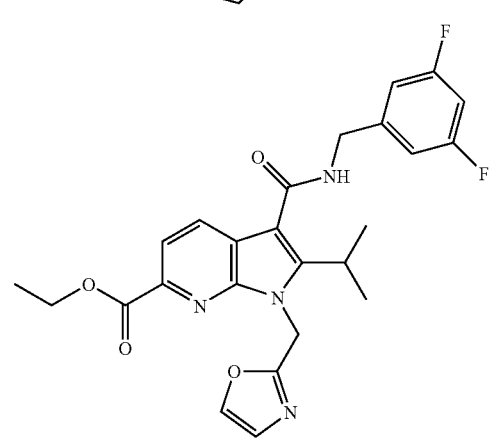

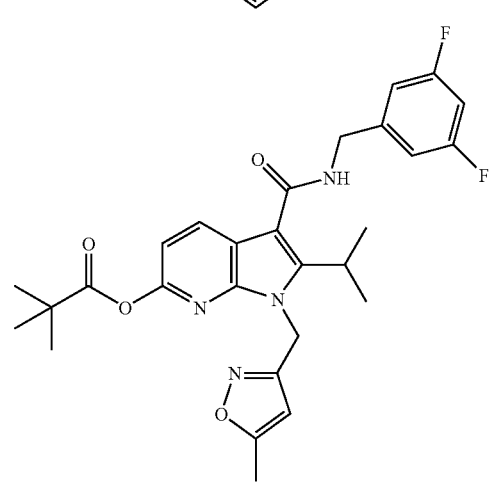

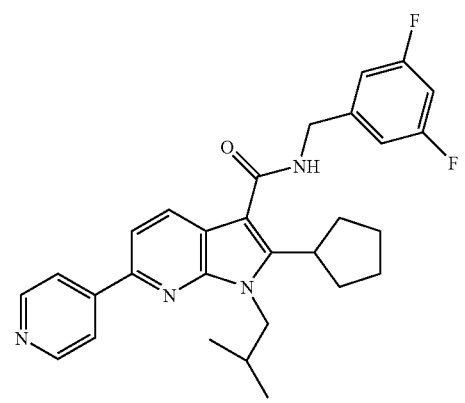
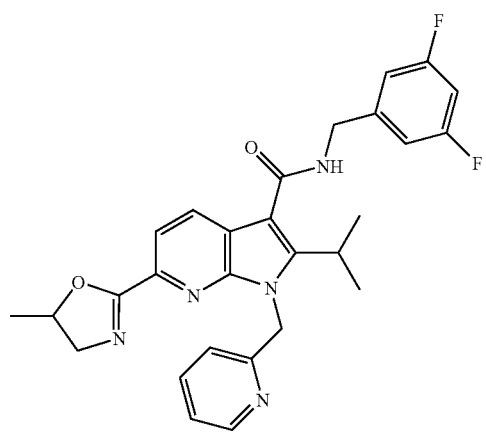
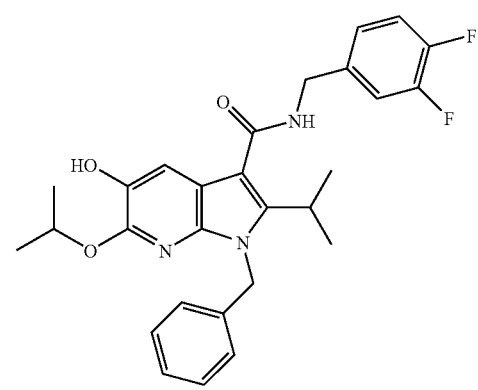
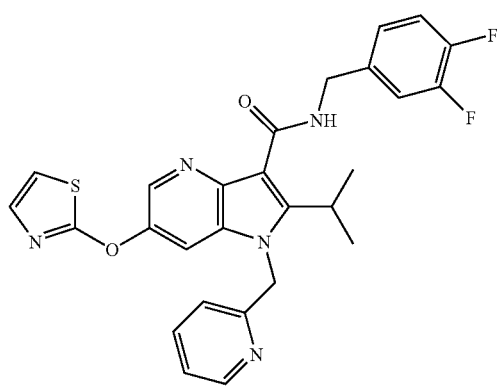
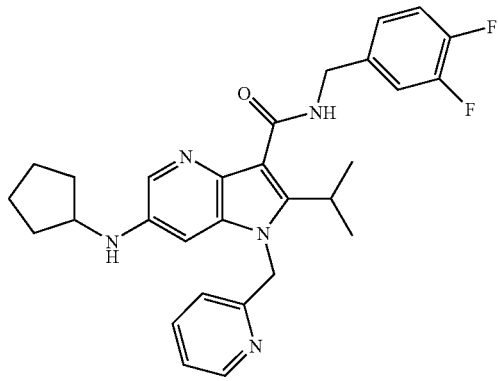
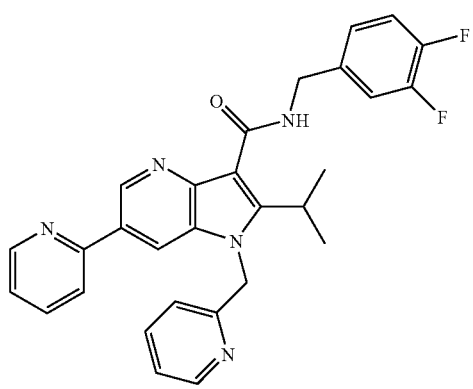
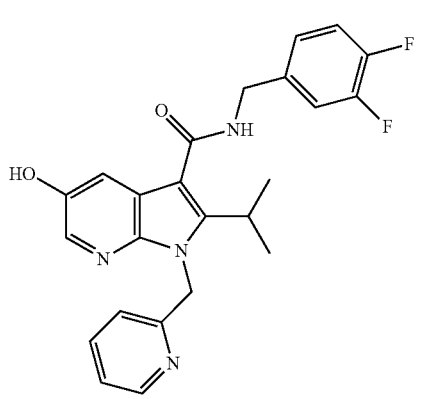
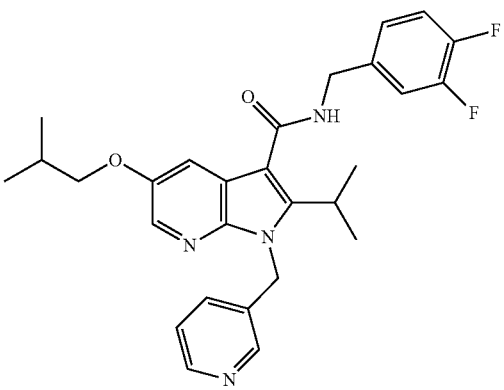

-continued
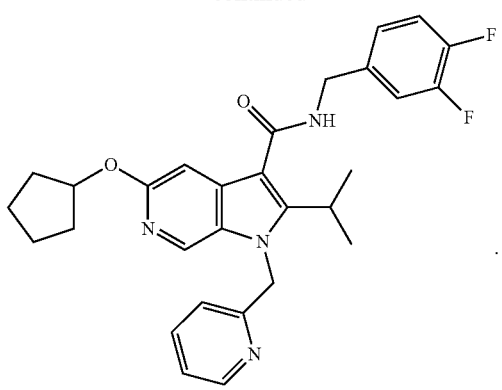
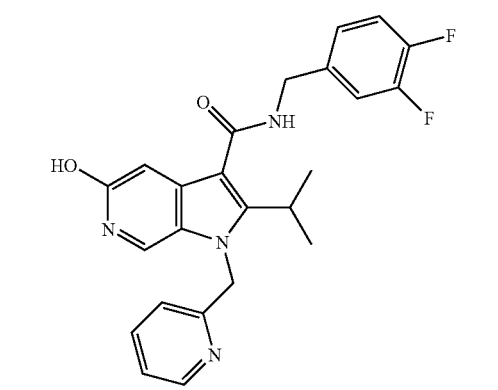
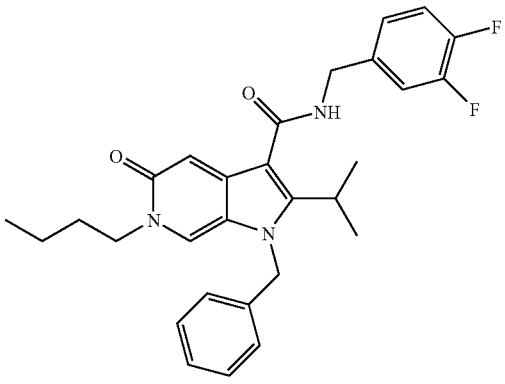
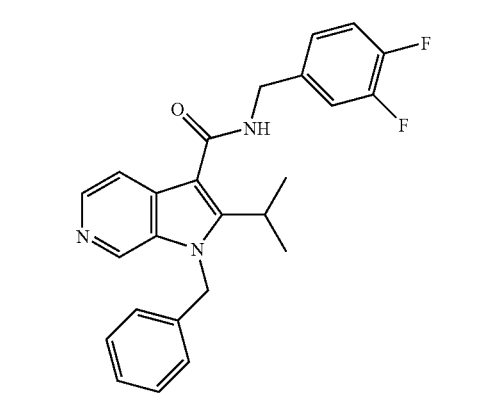
-continued
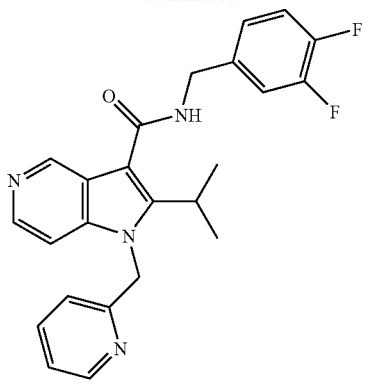
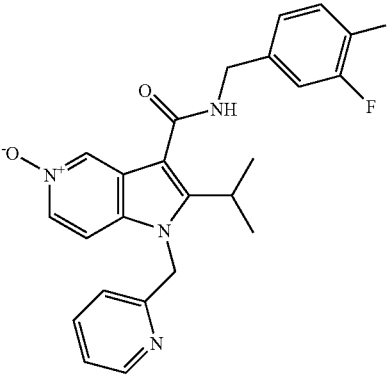
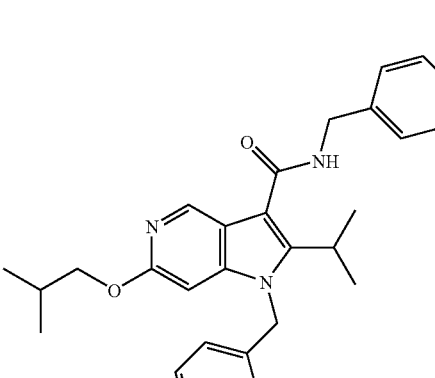
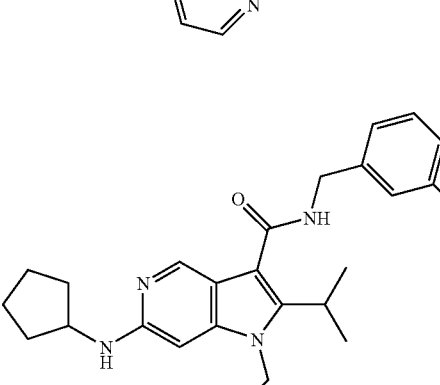

-continued

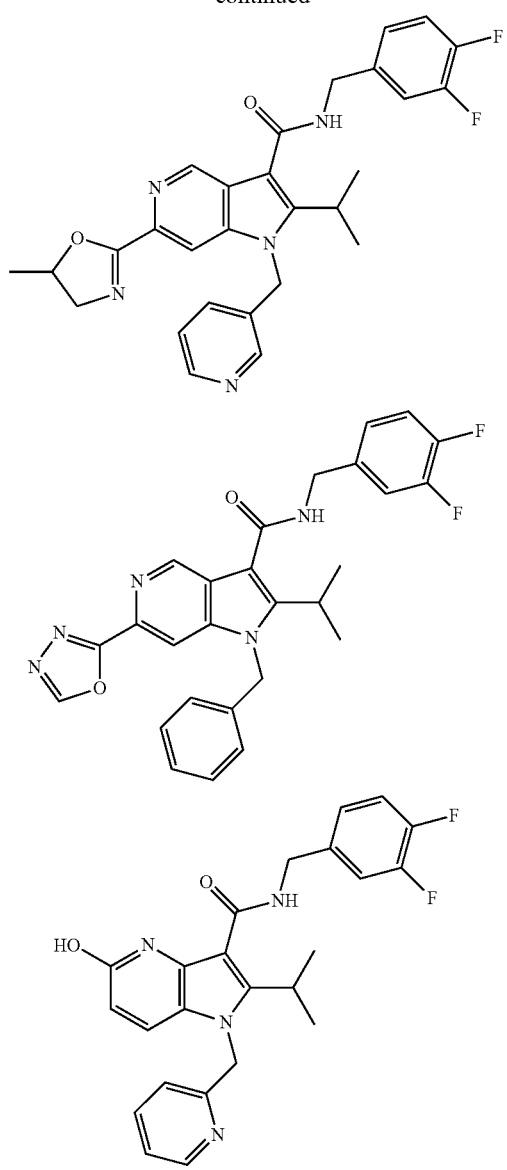

-continued

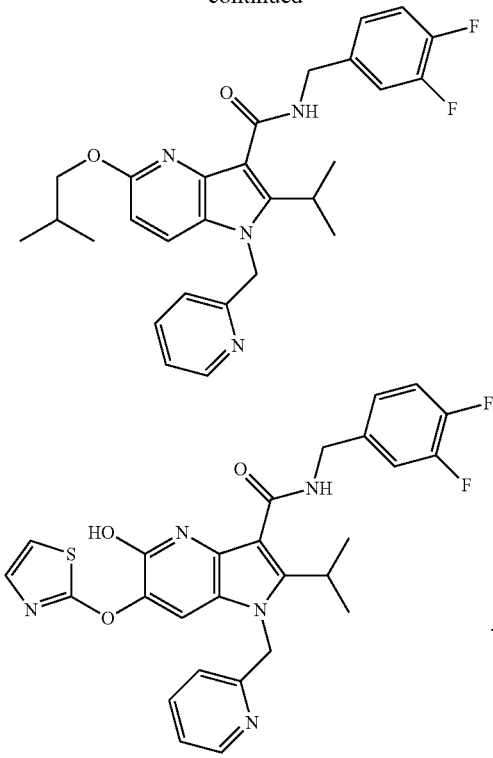

9. The compound of claim 1 selected from the group consisting of
1-Benzyl-2-isopropyl-5-methoxy-1H-pyrrolo[2,3-c]pyridine-3-carbaldehyde,
1-Benzyl-2-isopropyl-5-methoxy-1H-pyrrolo[2,3-c]pyridine-3-carboxylic acid,
1-Benzyl-N-(3,4-difluorobenzyl)-2-isopropyl-5-methoxy-1H-pyrrolo[2,3-c]pyridine-3-carboxamide,
1-Benzyl-N-(3,4-difluorobenzyl)-5-hydroxy-2-isopropyl-1H-pyrrolo[2,3-c]pyridine-3-carboxamide, 1-Benzyl-6-chloro-2-isopropyl-1H-pyrrolo[3,2-c]pyridine-3-carboxylic acid, and
1-Benzyl-6-chloro-N-(3,4-difluorobenzyl)-2-isopropyl-1H-pyrrolo[3,2-c]pyridine-3-carboxamide.

\* \* \* \* \*